United States Patent
Patzke et al.

(10) Patent No.: US 6,610,291 B2
(45) Date of Patent: Aug. 26, 2003

(54) READY-TO-USE RISTOCETIN COFACTOR TEST REAGENT POSSESSING LONG-TERM STABILITY

(75) Inventors: Jürgen Patzke, Marburg (DE); Konrad Braun, Ebsdorfergrund (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 09/739,649

(22) Filed: Dec. 20, 2000

(65) Prior Publication Data

US 2001/0006773 A1 Jul. 5, 2001

(30) Foreign Application Priority Data

Dec. 29, 1999 (DE) ........................................ 199 64 109

(51) Int. Cl.$^7$ ................................................ C12N 5/00
(52) U.S. Cl. .................... 424/93.72; 424/532; 435/40.5
(58) Field of Search ......................... 435/40.5; 424/532, 424/93.72

(56) References Cited

U.S. PATENT DOCUMENTS

| | | | |
|---|---|---|---|
| 4,145,185 A | 3/1979 | Brinkhous et al. | 436/69 |
| 4,302,355 A | * 11/1981 | Turner, Jr. et al. | 424/532 |
| 4,510,126 A | * 4/1985 | Fuhge et al. | |
| 5,827,741 A | 10/1998 | Beattie et al. | 435/374 |
| 6,127,111 A | 10/2000 | Braun | 435/2 |
| 6,221,575 B1 | 4/2001 | Roser et al. | 435/2 |
| 2002/0076445 A1 | 6/2002 | Crowe et al. | 424/532 |

FOREIGN PATENT DOCUMENTS

| | | | |
|---|---|---|---|
| DE | A-31 41 894 | 5/1983 | |
| JP | 2001131078 A2 | 5/2001 | A61K/35/14 |
| WO | WO 98/34478 | 8/1998 | A01N/1/02 |
| WO | WO 01/30141 | 5/2001 | A01N/1/02 |
| WO | WO 01/58266 | 8/2001 | A01N/61/00 |

OTHER PUBLICATIONS

Takahashi et al., Japanese Journal of Artificial Organs 26(3):637–640 (1997). Abstract.*

M.S. Read, et al., "Preservation of hemostatic and structural properties of rehydrated lyophilized platelets: Potential for long-term storage of dried platelets for transfusion," *Proc. Natl. Acad. Sci. USA*, 92:397–401 (1995).

A.P. Bode and M.S. Read, "Lyophilized platelets: continued development," *Transfus. Sci.*, 22(1–2):99–105 (Feb.–Apr., 2000).

H.A. Cooper, et al., "Proteolysis of human fixed, washed platelets by gram–negative bacterial metalloproteases: effect on von Willebrand factor–human platelet interactions," *Ann. N.Y. Acad. Sci.*, 370:179–90 (1981).

F. Rodeghiero, et al. "Von Willebrand Factor Antigen is Less Sensitive than Ristocetin Cofactor for the Diagnosis of Type I von Willebrand Disease–Results Based on an Epidemiological Investigation" *Thrombosis and Haemostasis* 64(3):349–352 (1990).

E.J. Gangarosa, et al. "Ristocetin–Induced Thrombocytopenia: Site and Mechanism of Action" *A.M.A. Archives of Internal Medicine* 105:83–89 (1960).

M.A. Howard and B.G. Firkin, "Ristocetin—A New Tool in the Investigation of Platelet Aggregation" *Thrombosis Diath. Haemostasis* 26:362–369 (1971).

H.J. Weiss, et al. "Quantitative Assay of a Plasma Factor Deficient in von Willebrand's Disease that is Necessary for Platelet Aggregation" *The Journal of Clinical Investigation* 52:2708–2716 (1973).

J.P. Allain, et al. "Platelets fixed with paraformaldehyde: a new reagent for assay of von Willebrand factor and platelet aggregating factor" *J. Lab.Clin. Med.* 85(2):318–328 (1975).

K.B. Thomas, et al. "Parallel Determination of von Willebrand Factor Ristocetin and Botrocetin Cofactors" *Thrombosis Research* 75(4):401–408 (1994).

J. Stribbe and E.P. Kirby "The Influence of Haemaccel, Fibrinogen and Albumin on Ristocetin–induced Platelet Aggregation. Relevance to the Quantitative Measurement of the Ristocetin Cofactor" *Thrombosis Research* 8: 151–165 (1976).

J. Rivera et al., "Stability of Glycoproteins Ib/IX and IIb/IIIa during Preparation and Storage of Platelet Concentrates: Detection by Binding Assays with Epitope–Defined Monoclonal Antibodies and Physiological Ligands," *Vox Sang*, 67: 166–71 (1994).

\* cited by examiner

*Primary Examiner*—Jean C. Witz
(74) *Attorney, Agent, or Firm*—Finnegan, Henderson, Farabow, Garrett and Dunner, L.L.P.

(57) ABSTRACT

The present invention relates to a ready-to-use ristocetin cofactor test reagent possessing long-term stability for use in coagulation tests.

18 Claims, 9 Drawing Sheets

READY-TO-USE RISTOCETIN COFACTOR TEST REAGENT POSSESSING LONG-TERM STABILITY

The present invention relates to a ready-to-use ristocetin cofactor test reagent possessing long-term stability for use in coagulation tests.

The von Willebrand-Jürgens syndrome is the most frequently occurring hemorrhagic diathesis. The von Willebrand protein (vWF) is quantitatively diminished, or its function is disturbed, in 1% of the population. A variety of tests are carried out for diagnosing the disease and its different forms. The ristocetin cofactor test (vWF:RCo) has become established as the most important screening test (Rodeghiero F. et al., Thromb. Haemost (1990) 64, pages 349–352). According to investigations carried out by Rodeghiero (1990), it has a sensitivity of 50% whereas the second most important test, i.e. determination of vWF antigen (vWF:Ag), only has a sensitivity of 32%.

Ristocetin is an antibiotic which was rapidly withdrawn from the market because of its powerful side-effects. Gangarosa et al. (Gangarosa E J et al., Arch. Intern. Med. (1960), pages 83–89) discovered in 1960 that ristocetin causes rabbit platelets to aggregate in vitro. While human platelets in platelet-rich plasma (PRP) also aggregate in the presence of ristocetin, they do not do so in the case of patients suffering from von Willebrand syndrome (Howard and Firkin, Thromb. Diath. Haemorrh (1971), 26, pages 362–369). Based on these observations, Weiss et al., (Weiss H J et al., J. Clin. Invest. (1973) 52, pages 2708–2716) developed a quantitative test using washed platelets from healthy donors. However, the washed platelets can only be used for a few hours. Use has also been made of fixed platelets, which have the advantage of retaining their activity for a relatively long period of time, resulting in there being less need for the elaborate working-up of fresh PRP (Allain JP et al., J. Lab. Clin. Med. (1975), 85, pages 318–328).

The ristocetin cofactor test resembles the in-vivo function of the protein, for which reason the test is frequently termed an activity test. When added to a test mixture containing platelets and von Willebrand factor, ristocetin induces binding of the vWF molecule to the GPIb/V/IX receptor and consequently agglutination of the platelets. The precise mode of action is still not known. Ristocetin evidently binds to vWF, and it is assumed that a crucial reaction is the change in the conformation of the vWF molecule which is elicited by the binding of ristocetin, with this conformational change then enabling the vWF molecule itself to bind to GPIb/V/IX. This process would be comparable to the change in conformation which is due to binding to the subendothelium and which makes the vW factor able to bind in vivo (particularly at high shearing forces).

Available values for the stability of fixed platelets in relation to vWF:Rco activity during liquid storage vary between 1 month (Allain et al., J. Lab. Clin. Med. 1975, 85, pages 318–328) and up to 6 months (Thomas et al. (1994), Thromb. Res. 75, 4, pages 401–408).

However, a stability of at least 10 months, and even better at least 14 months, is necessary for commercial use.

It has previously only been possible to achieve a substantial improvement in stability by lyophilizing the platelets (U.S. Pat. No. 4,145,185, DE 3141894A1). In this connection, U.S. Pat. No. 4,145,185 describes adding a snake venom. DE 3131894 describes using a tanning agent, a serine proteinase inhibitor and ristocetin A.

The platelet reagents for the ristocetin cofactor test which are currently available commercially are all lyophilized. Particularly when using such a lyophilized reagent in a fully automated or partially automated analytical appliance, it is a disadvantage that the product cannot be used directly after opening; the lyophilizate has first of all to be reconstituted. In addition to this, lyophilization is an expensive procedure which, furthermore, simply because of the additional procedural steps, associated both with preparing the lyophilizate and using it, harbors the danger of additional errors and damage to the platelets. When lyophilized reagents are used, a relatively large divergence in the results, arising from the preparation procedure, can often be observed from vial to vial within one production batch.

The object underlying the present invention was therefore to make available a process for the ristocetin cofactor test using a liquid formulation of a platelet reagent which enables the liquid reagent to be used even after a storage time of significantly more than 6 months, preferably at least 10 months, particularly preferably at least 14 months, i.e. such that the specifications of the test, such as measurement range and precision, are met when the reagent is used in a test even after this storage time.

Such a reagent is extremely advantageous for a coagulation laboratory since it combines the advantages of being easy to handle (being ready to use) with the advantages of high sensitivity and good reproducibility. Other preferred embodiments of the invention can also be found in the patent claims.

Figure 2:
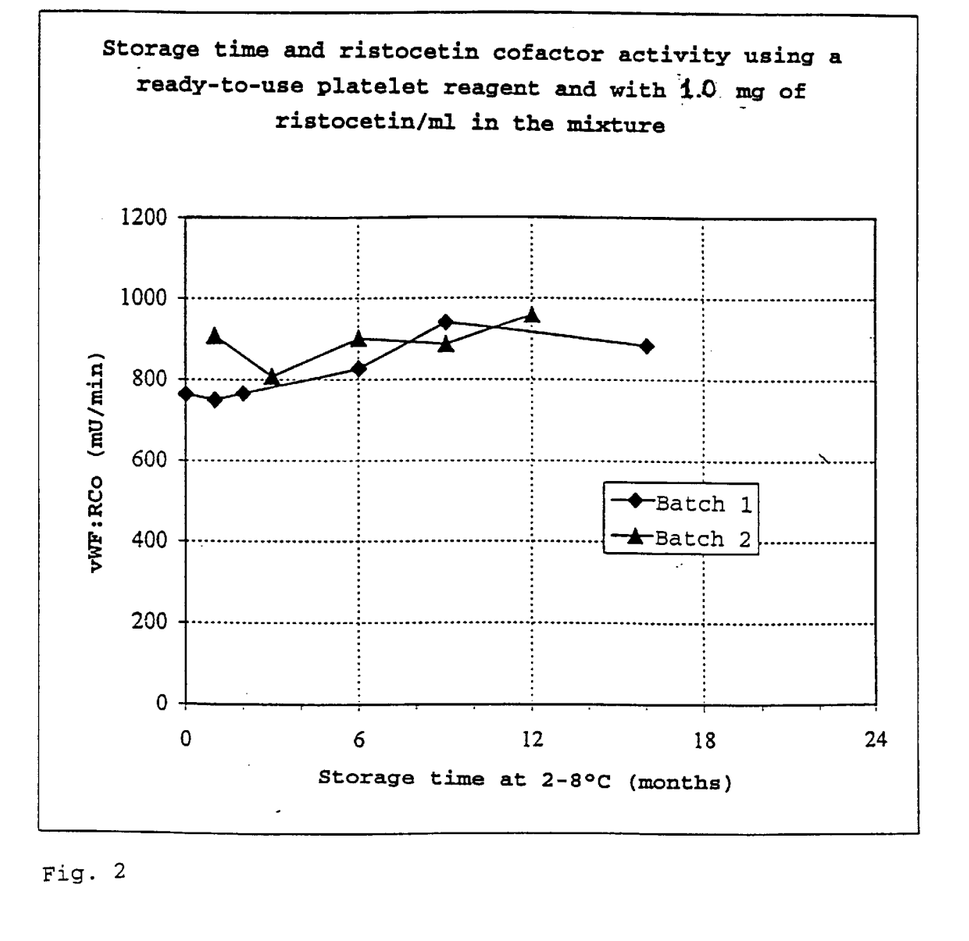

It has now been found, surprisingly, that a stability of 12 months or more can be achieved in a ready-to-use (approximately 600,000 platelets/$\mu$l) liquid preparation if, when being worked up, the platelets are treated with a serine protease inhibitor (preferably diisopropyl fluorophosphate), fixed and suspended in an aqueous, buffered solution which does not contain any ristocetin or snake venom (FIG. 2).

The storage stability can be improved, inter alia, by adding neutral proteins, such as albumins, in particular human or bovine serum albumin. When the albumin concentration is adequate (greater than 0.2%, preferably 2%), ristocetin can also be added to the liquid preparation.

The storage stability can be substantially improved, even when ristocetin is present, by treating the liquid preparation with, or adding to it, an isothiazolone, such as KATHON, preferably Kathon® CG (Rohm & Haas, Philadelphia, USA), or PROCLIN, or another bactericidal or bacteriostatic substance. Advantageously, these compounds are employed in the reagent at a concentration (vol/vol) of from 0.1 to 2%, particularly advantageously of from 0.5 to 1.4%, very particularly advantageously of from 0.8 to 1.2%.

Other additives which are known to the skilled person, and which are described, for example, in DE 3141894, have an additionally advantageous effect on the long-term stability during liquid storage.

Unless otherwise indicated, the term storage and like terms refer to storage at 2–8° C. (refrigerator) and the term stability and the like refers to determining the vWF:RCo test (Thomas et al. (1994)).

According to the known state of the art, a poorer shelf-life would be expected if the reagent was stored with a concentration of platelets which enabled it to be used directly for the test without dilution (ready-to-use) than if the reagent was stored as a concentrate. A concentrate typically contains 5–15 million platelets/$\mu$l. In fact, the reagent according to the invention has a shelf-life of more than 12 months (FIG. 1) even when it contains only 600,000 platelets/$\mu$l (FIG. 2).

Figure 3:
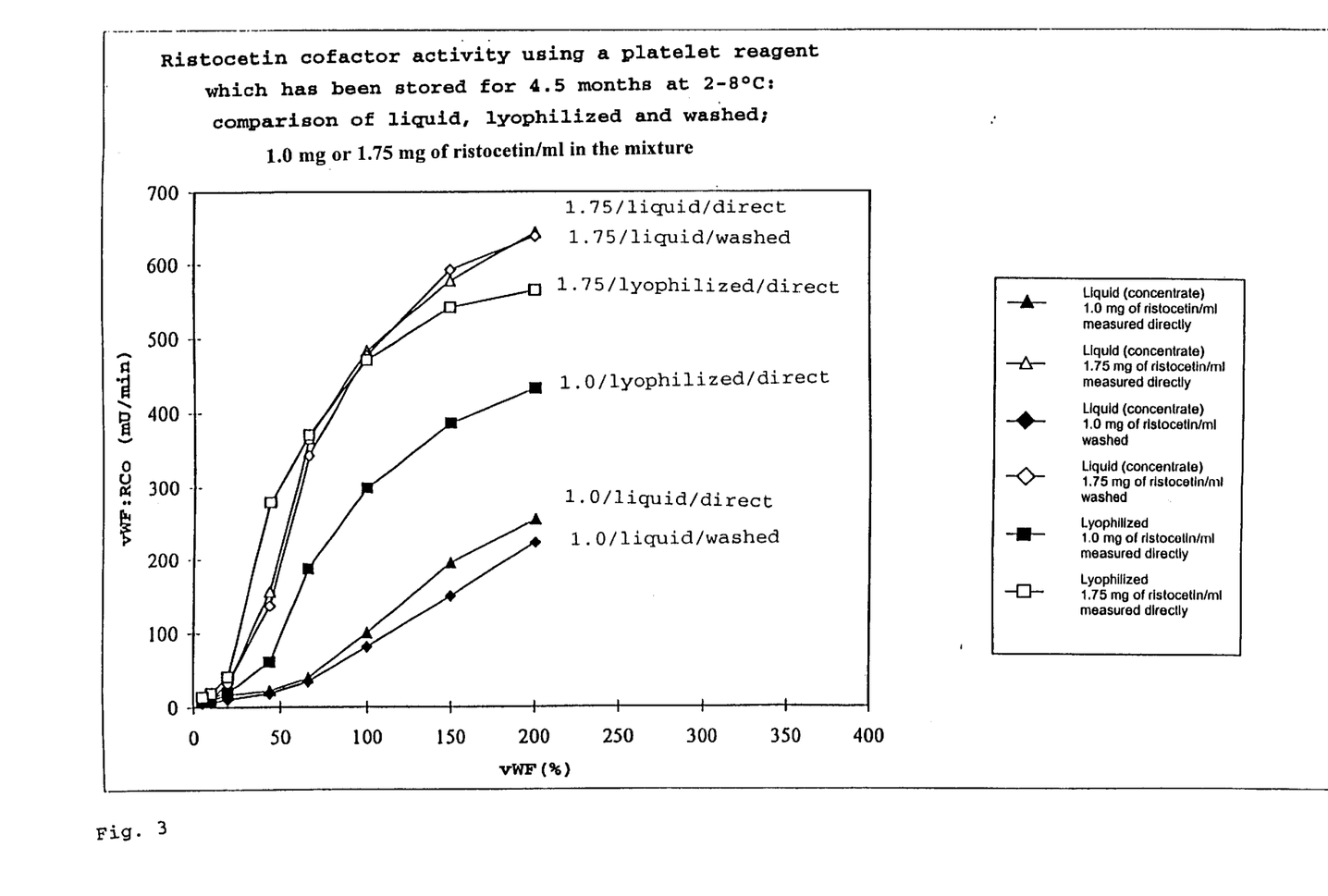
Figure 9:
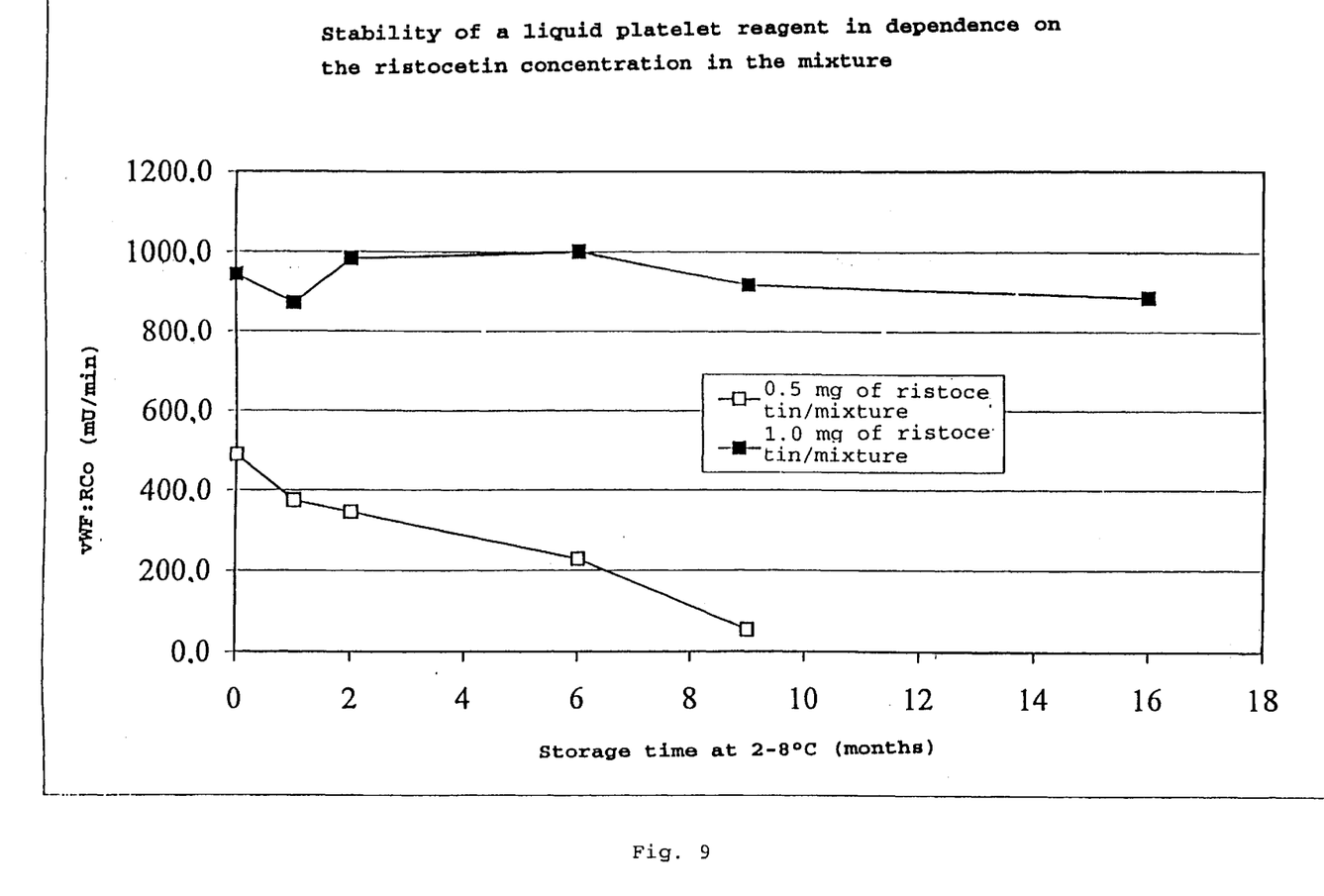

Independently of the nature of the reagent, it was furthermore found that increasing the concentration of ristocetin in the test mixture to more than 1.25 mg/ml (independently of how much albumin is present in the reagent or the test mixture) can have a positive influence on the usability of platelet reagent which has been stored for a long time. A reagent which is no longer active enough when the concentration of ristocetin in the test mixture is 1.0 mg/ml may exhibit adequate activity when a ristocetin concentration of, for example, 1.5 mg/ml is used, and may not show any loss of activity, either, during the course of its lifetime (FIGS. 3, 4 and 9).

An example of this positive effect of an increase in the concentration of ristocetin in the test mixture is storage of a platelet concentrate (100 ml) in an Erlenmeyer flask (250 ml) which was opened for withdrawing reagent at the measurement time and then sealed once again. The frequent opening results in extensive contact with the air and a high risk of contamination. When the usual ristocetin concentration of 1.0 mg/ml was used in the test mixture, the reactivity of the platelets, that is the ristocetin cofactor activity, had fallen markedly after 4.5 months of storage. While no initial value was determined in this case, the activity of the concentrate can also be compared with the activity of lyophilized platelets (the same batch), which are known to be very stable (FIG. 3). When a comparison is made between liquid storage and freeze drying, a marked loss of reactivity is seen after 4½ months of storage when the ristocetin concentration in the mixture is 1.0 mg/ml while, by contrast, no significant difference in reactivity is seen when the ristocetin concentration in the mixture is 1.75 mg/ml (FIG. 3). The harmful effect of storing in the Erlenmeyer flask (contact with the air, contamination, aging) is consequently compensated for by the higher concentration of ristocetin. This storage effect is presumably also the explanation for the relatively sharp fall in reactivity in this measurement as compared with the results from the experiment depicted in FIG. 2.

Another example of the positive effect of an increase in ristocetin concentration in the test mixture is seen when reagent is prepared by the method described by Thomas et al. (1994), which method is claimed to lead to a reagent which is stable for 6 months. After 18 months, the activity of this reagent is, as would be expected, seen to have decreased very markedly when 1.0 mg of ristocetin is used in the test mixture. However, when 1.5 mg of ristocetin is used in the test mixture, the reactivity has not decreased to anything like the same extent (FIG. 4, paraformaldehyde as the fixative).

Figure 4:
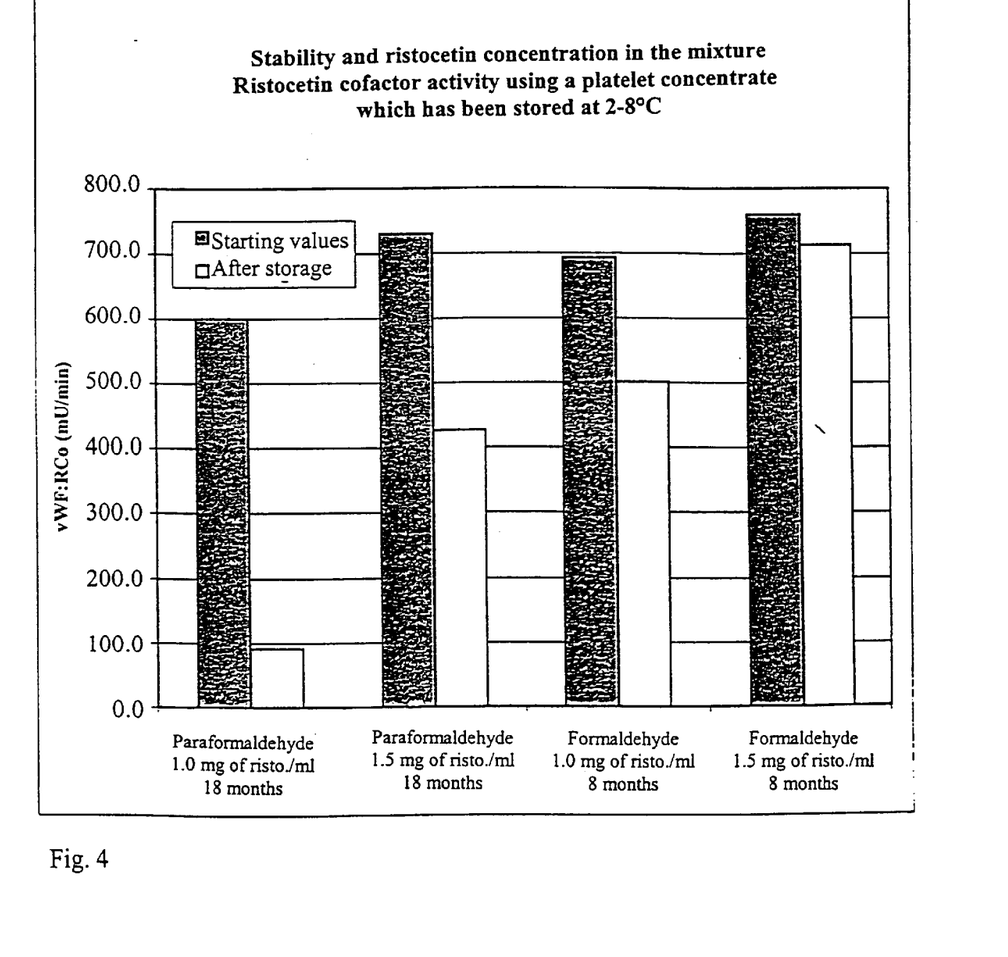

The fall in reactivity when fixing with formaldehyde solution and storing for 8 months is not so great, either, when 1.5 mg of ristocetin are used in the test mixture (FIG. 4).

The higher concentration of ristocetin consequently compensates for aging processes. If storage is unfavorable, these aging processes can also occur if the platelets have been previously treated with DFP (FIG. 3) or when a reagent of the state of the art is used (Thomas et al., 1994, (FIG. 4)).

Advantageously, it is also possible to choose to have a higher ristocetin concentration in the test mixture in combination with the reagent according to the invention.

The concentration of ristocetin in the test mixture is preferably from 1 to 2.4 mg/ml, particularly preferably from 1.25 to 2 mg/ml.

The reason for the increased requirement for ristocetin could also be the increase which occurs in the concentration of protein in the buffer over time, since it is known that ristocetin binds to a variety of proteins and that an increased protein concentration can be compensated for by adding more ristocetin (Stibbe and Kirby, Thromb. Res. (1976), 8, pages 151–165). Platelets which had been stored for 4½ months were therefore washed and taken up in fresh buffer (which once again contained ristocetin). The washing did not result in any change in activity either at 1.0 mg or at 1.75 mg of ristocetin/ml in the test mixture. It can be concluded from this that the aging process does in fact act on the platelets themselves (FIG. 3). Evidently, the aging decreases the sensitivity of the platelets to the effect of ristocetin. This is surprising to the extent that, until now, the main effect of ristocetin in the ristocetin cofactor test has been regarded as being some type of activation of the von Willebrand protein which makes the protein able to bind the GPIb receptor. However, if aged platelets require more ristocetin in order to exhibit the same agglutination activity, it is evident that direct interaction between ristocetin and platelets is more important for the ristocetin cofactor test than has previously been assumed.

Figure 5:
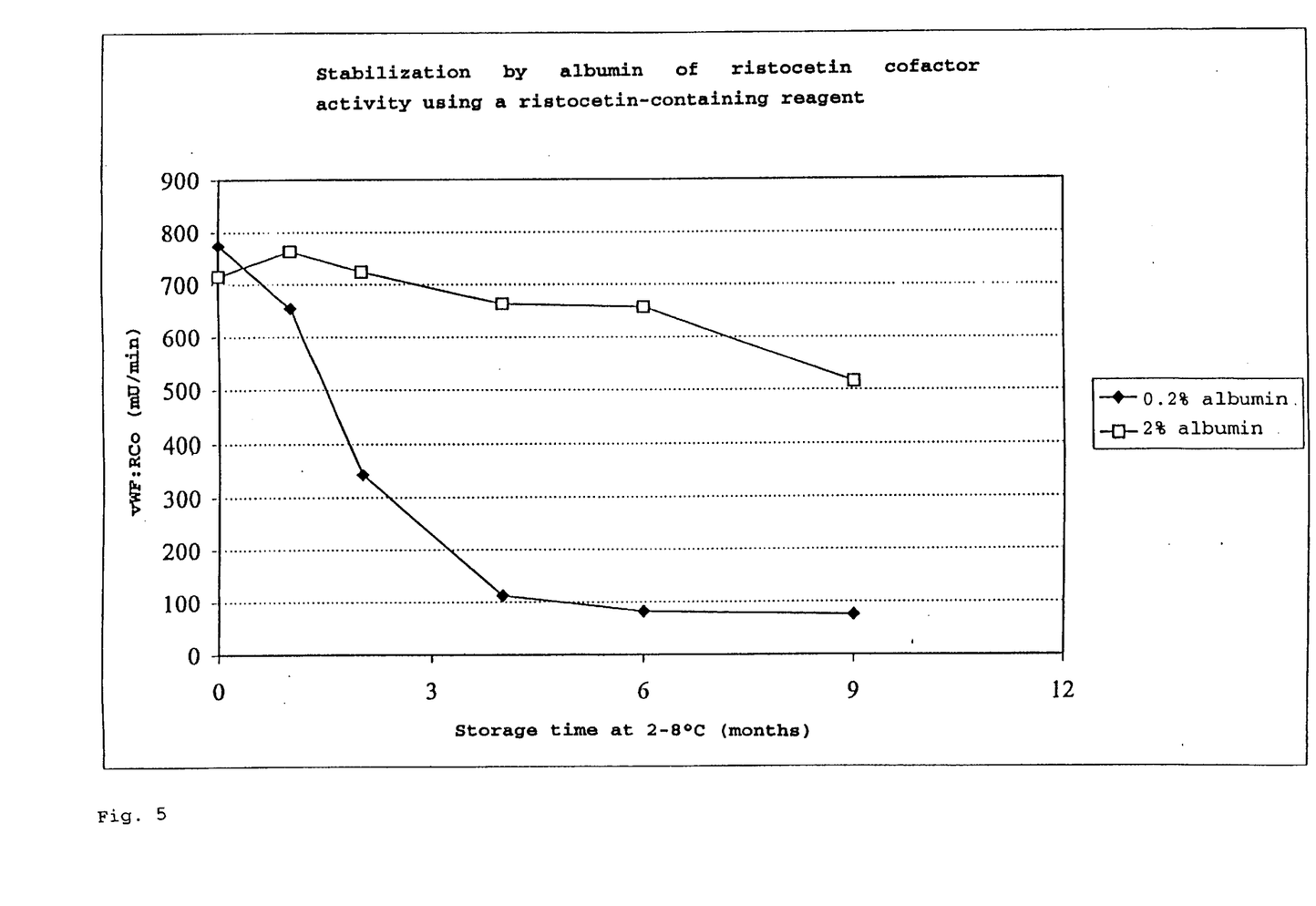

If ristocetin is already added to the platelet reagent while it is being stored, the reagent is then less stable than without ristocetin. However, its stability can be improved substantially by adding a neutral protein, preferably albumin, very preferably human or bovine albumin, to a concentration of more than 1%. Thus, its stability in the presence of 2% albumin is better than in the presence of 0.2% albumin (FIG. 5).

Figure 6:
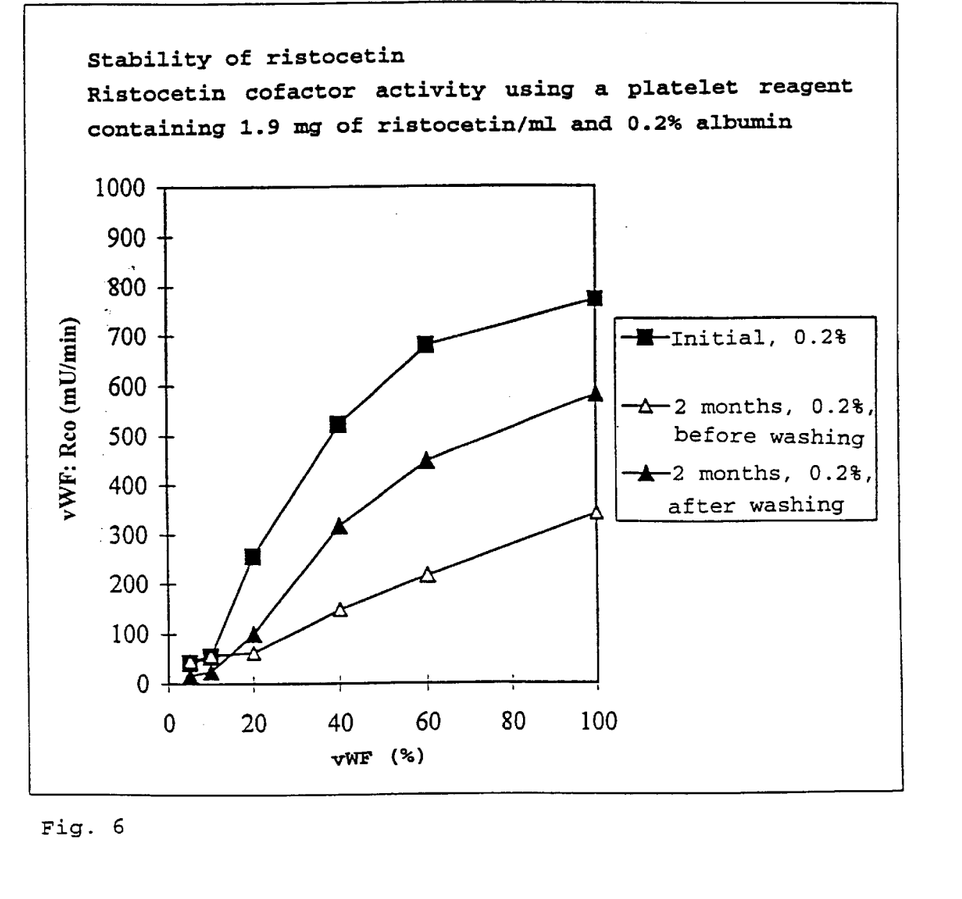

If platelets which have been stored in the presence of 0.2% albumin and ristocetin are washed with fresh buffer which also contains 0.2% albumin and ristocetin, their reactivity does increase once again but does not return to the starting level (FIG. 6, left-hand diagram). It can consequently be concluded from this that the platelets themselves have aged.

It is known from the literature that ristocetin precipitates fibrinogen and other proteins. This reaction is already discernible at a concentration of 0.5 mg/ml, and at a concentration of 2.0 mg/ml all the fibrinogen in the plasma has been precipitated while the other plasma proteins have not yet been affected (Howard and Firkin, Thromb. Diath. Haemorrh. (1971), 26, pages 362–369).

Figure 7:
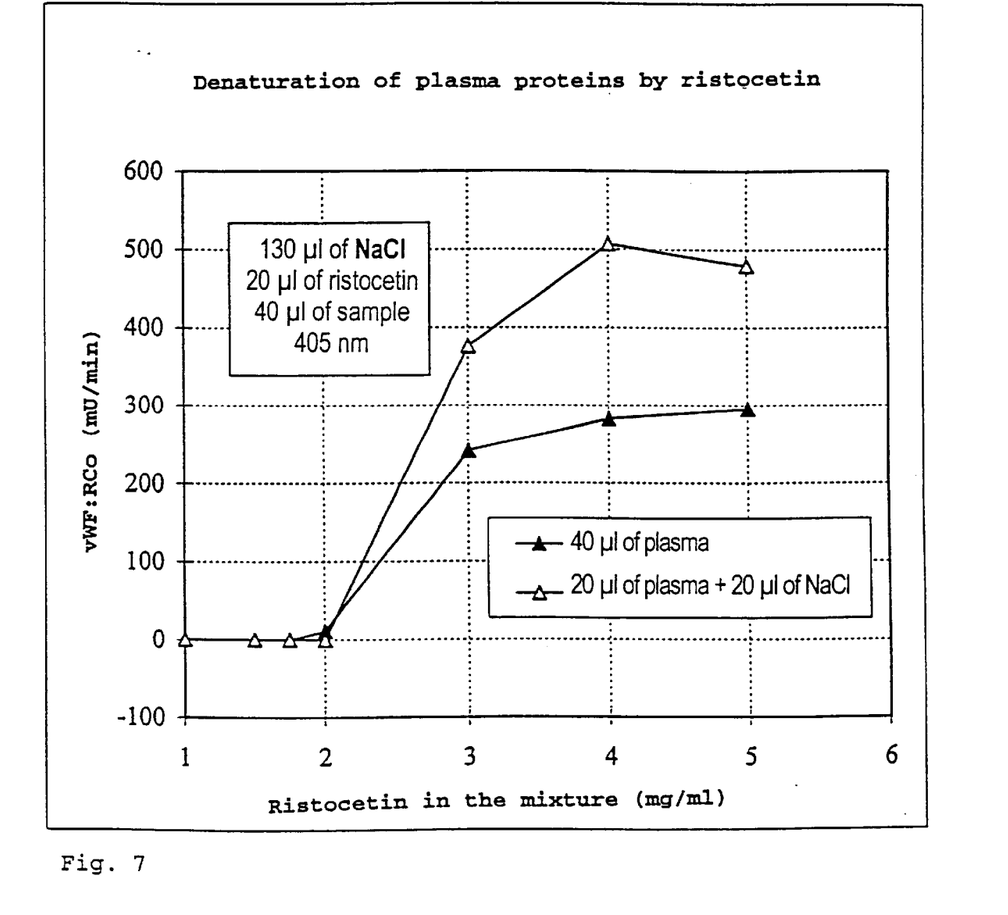

It was found that no interfering precipitation of protein occurs in the process according to the invention up to and including a ristocetin concentration in the mixture of 1.75 mg/ml (40 μl sample in 190 μl of test mixture) and 2.0 mg/ml (20 μl of sample in 190 μl of test mixture), respectively (FIG. 7).

Figure 8:
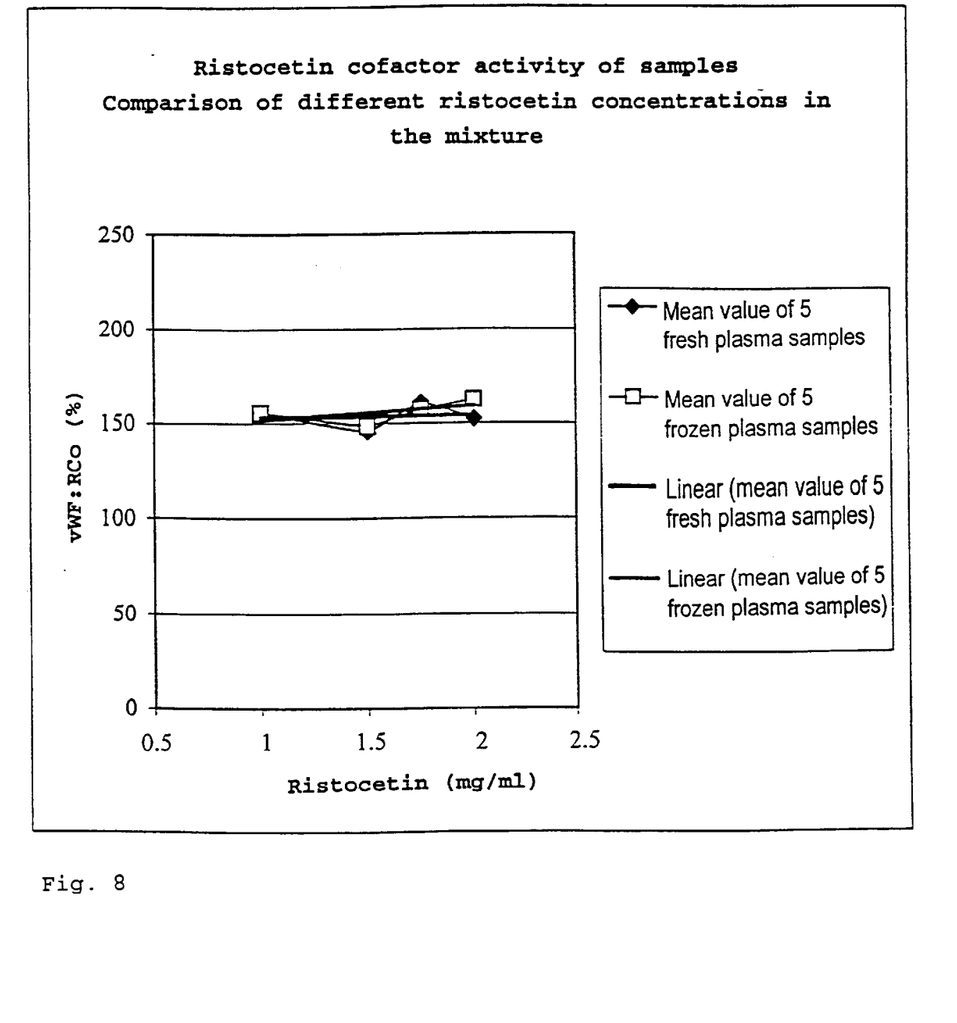

At ristocetin concentrations of up to 2.0 mg/ml, no significant differences in the results were observed when measuring samples in the vWF:RCo test (FIG. 8). The normal concentration of ristocetin in a vWF:RCo test mixture using fixed platelets is 1 mg/ml (Thomas et al. 1994: 1.0 mg/ml).

DESCRIPTION OF THE FIGURES

FIG. 1

Stability of a platelet concentrate reagent which was prepared using either DFP as in Example 1 or without using DFP, as in Thomas et al., (1994), Thromb. Res. 75, 4, pages 401–408.

FIG. 2

Stability of a ready-to-use platelet reagent containing 600,000 platelets/μl.

FIG. 3

Activity of a platelet concentrate reagent which has been stored for 4.5 months when the test mixture contains 1.75 and 1.0 mg of ristocetin/ml, respectively.

FIG. 4

Effect of the concentration of ristocetin in the test mixture on the activity of the reagent after 18 and 8 months of storage, respectively. The reagent was worked up with paraformaldehyde as described in Thomas et al., (1994), Thromb. Res. 75, 4, pages 401–408, while it was worked up with formaldehyde as described in Example 1. The ristocetin concentration given refers to the test mixture.

FIG. 5

Stability of a ristocetin-containing platelet reagent which additionally contains either 0.2% or 2% albumin.

FIG. 6

Fall in the reactivity, at various concentrations of von Willebrand protein, of a platelet reagent containing ristocetin and 0.2% albumin after 2 months. After the platelets have been washed with fresh buffer of the same composition as at the beginning of the storage period, their reactivity increases somewhat once again.

FIG. 7

Precipitation of proteins from the sample by high concentrations of ristocetin.

FIG. 8

Effect of high concentrations of ristocetin on measurement of the concentration of von Willebrand protein using the ristocetin cofactor test.

FIG. 9

Fall in the reactivity of a platelet reagent when the test mixture contains 0.5 and 1.0 mg of ristocetin/ml, respectively.

The following examples clarify the invention.

EXAMPLE 1

Platelets were isolated from whole blood by centrifuging off the erythrocytes. The isolated platelets were then washed three times by taking them up in phosphate buffer A (0.07 mol of phosphate/l, 8.5 g of NaCl/l, 1.9 g of EDTA/l) and then centrifuging them; the number of platelets was adjusted to approx. 3 million/µl.

After diisopropyl fluorophosphate had been added (DFP, 4.5×10 U–4M), the platelets were incubated at room temperature for 1 hour while being stirred. After the platelets had been washed twice by being centrifuged and taken up once again in phosphate buffer B (0.15 mol of phosphate/l, 1.0 g of EDTA/l, pH 6.5), the platelets were then incubated, after formaldehyde had been added (final concentration 4%), at 4° C. for 44 hours. The platelets were centrifuged and taken up in phosphate buffer C (0.07 mol of phosphate/l, 8.5 g of NaCl/l, 1.0 g of EDTA/l, 1 g of sodium azide/l).

The platelet suspension was then dialyzed against the 20-fold volume of phosphate buffer C for a period of approx. 24 hours. After that, the platelet count was adjusted by adding phosphate buffer C. The following were also added: sucrose (10 g/l), glycine (10 g/l), glutamate (16.7 g/l) and human albumin (2 g/l).

The platelet reagent was then used to fill 5 ml vials which were fitted with airtight screw caps.

Prior to the measurement (absorbance in mU), 0.5 ml of ristocetin solution (21 mg/ml) was added to the 5 ml contents of a vial so that the concentration of ristocetin in the reagent was consequently 1.91 mg/ml. The composition of the test mixture was as follows:

150 µl of reagent
20 µl of plasma and
20 µl of isotonic NaCl solution (0.9%)

The rate of decrease in the extinction ($V_{max}$) was measured. The concentration of ristocetin in the test mixture was 1.5 mg/ml.

EXAMPLE 2

Figure 1:
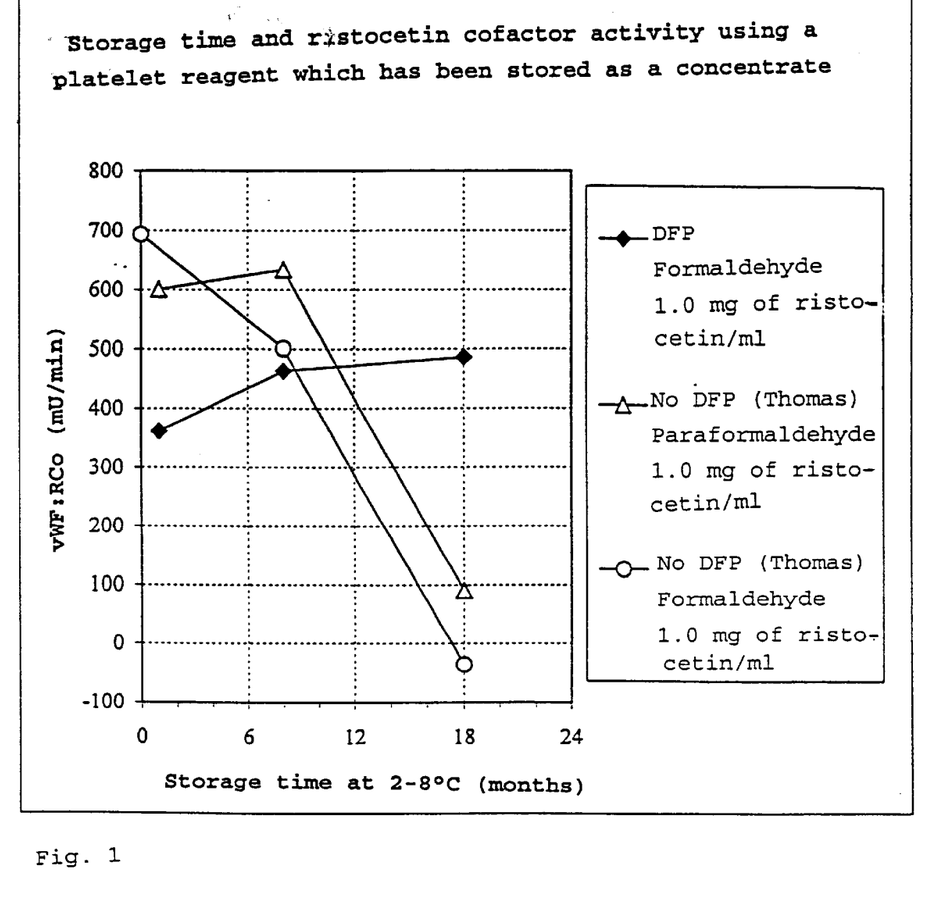

This example was implemented as described in Example 1, except that the concentration of ristocetin in the platelet reagent was adjusted to 1.3 mg/ml prior to the measurement and the concentration of ristocetin in the test mixture was consequently 1.0 mg/ml (FIGS. 1, 2 and 9).

EXAMPLE 3

This example was implemented as described in Example 1, except that the concentration of ristocetin in the platelet reagent was adjusted to 2.2 mg/ml prior to the measurement and the concentration of ristocetin in the test mixture was consequently 1.75 mg/ml (FIG. 3).

EXAMPLE 4

This example was implemented as described in Example 1, except that sufficient ristocetin was added to the platelet reagent before it was used to fill the 5 ml vials fitted with airtight screw caps to ensure that the final concentration in the reagent was 1.9 mg/ml. This corresponds to a concentration of ristocetin in the test mixture of 1.5 mg/ml (FIG. 5).

What is claimed is:

1. A liquid preparation comprising a suspension of fixed platelets, wherein the liquid preparation is not lyophilized prior to use and is capable of remaining stable for at least 10 months after storage in the liquid state, and wherein, during the process of making the liquid preparation, the platelets are treated with a serine protease inhibitor, fixed, and suspended in an aqueous solution which contains at least one neutral protein and does not contain any ristocetin or snake venom.

2. The preparation as claimed in claim 1 which exhibits a reactivity of at least 80% of the starting value as measured in a ristocetin cofactor test after storage in the liquid state for at least 12 months.

3. The preparation as claimed in claim 1 for measuring and quantifying von Willebrand factor.

4. The preparation as claimed in claim 1 in the form of a ready-to-use (approximately 50,000–2,000,000 platelets/µl) preparation.

5. The preparation as claimed in claim 4 containing 200,000–1,000,000 platelets/µl.

6. A test kit for a ristocetin cofactor test, which kit contains the preparation as claimed in any one of claims 1 to 4.

7. A test kit for a ristocetin cofactor test, which kit contains the preparation as claimed in claim 5.

8. A ristocetin cofactor test comprising the preparation as claimed in any one of claims 1 to 4 in which the concentration of ristocetin in the test mixture is from 1 to 2.4 mg/ml.

9. The ristocetin cofactor test according to claim 8 in which the concentration of ristocetin in the test mixture is from 1.25 to 2 mg/ml.

10. A ristocetin cofactor test comprising the preparation as claimed in claim 5 in which the concentration of ristocetin in the test mixture is from 1 to 2.4 mg/ml.

11. The ristocetin cofactor test according to claim 10 in which the concentration of ristocetin in the test mixture is from 1.25 to 2 mg/ml.

12. The preparation as claimed in claim 1, wherein the aqueous solution buffered.

13. The preparation as claimed in claim 1, wherein the liquid preparation of fixed platelets is capable of remaining stable for at least 12 months after storage in the liquid state.

14. The preparation as claimed in claim 5, containing approximately 600,000 platelets/$\mu$l.

15. The preparation as claimed in claim 1 wherein said at least one neutral protein comprises an albumin.

16. The preparation as claimed in claim 15 wherein the albumin is bovine serum albumin.

17. The preparation as claimed in claim 15 wherein the albumin is human albumin.

18. The preparation as claimed in claim 1, wherein the preparation is suitable for commercial use.

* * * * *